US010265070B2

(12) United States Patent
Chen et al.

(10) Patent No.: US 10,265,070 B2
(45) Date of Patent: Apr. 23, 2019

(54) LINEAR CUTTING STAPLER

(71) Applicant: Suzhou Touchstone International Medical Science Co., Ltd., Suzhou (CN)

(72) Inventors: Wangdong Chen, Suzhou (CN); Tuo Shu, Suzhou (CN); Yongwang Pei, Suzhou (CN)

(73) Assignee: Suzhou Touchstone International Medical Science Co., Ltd., Suzhou (CN)

( * ) Notice: Subject to any disclaimer, the term of this patent is extended or adjusted under 35 U.S.C. 154(b) by 378 days.

(21) Appl. No.: 15/108,896

(22) PCT Filed: Dec. 26, 2014

(86) PCT No.: PCT/CN2014/095149
§ 371 (c)(1),
(2) Date: Jun. 29, 2016

(87) PCT Pub. No.: WO2015/101226
PCT Pub. Date: Jul. 9, 2015

(65) Prior Publication Data
US 2017/0209143 A1    Jul. 27, 2017

(30) Foreign Application Priority Data

Dec. 31, 2013  (CN) .......................... 2013 1 0749269
Dec. 31, 2013  (CN) ...................... 2013 2 0887855 U

(51) Int. Cl.
*A61B 17/072*    (2006.01)
*A61B 90/00*    (2016.01)

(52) U.S. Cl.
CPC ........ *A61B 17/07207* (2013.01); *A61B 90/03* (2016.02); *A61B 2017/07271* (2013.01);
(Continued)

(58) Field of Classification Search
CPC .... A61B 17/07207; A61B 2017/07271; A61B 2017/07285; A61B 2017/07278;
(Continued)

(56) References Cited

U.S. PATENT DOCUMENTS 4,569,346 A    2/1986 Poirier
4,809,898 A    3/1989 Gassner et al.
(Continued)

FOREIGN PATENT DOCUMENTS

CN    101756738 A    6/2010
CN    101797174 A    8/2010
(Continued)

*Primary Examiner* — Robert Long
(74) *Attorney, Agent, or Firm* — Fox Rothschild LLP

(57) ABSTRACT

A linear stapling and severing apparatus comprises upper and lower jaws, the lower jaw comprises a staple cartridge holder, a staple cartridge is arranged on the staple cartridge holder in a detachable way, and a cutter us movably arranged inside the staple cartridge. The apparatus also comprises a safety piece installed on the staple cartridge in an upper-and-down movable way. The cutter comprises a slot and a butting part. When the cutter is located are a near end of the staple cartridge and in a non-locked state, the safety piece prevents the safety piece from entering the slot. The cutter can complete a stapling and severing process. When the cutter goes back to the near end it is in a locked state, the safety piece is located at a second position that is clamped inside the slot to restrict movement of the cutter.

19 Claims, 6 Drawing Sheets

(52) U.S. Cl.
CPC .............. *A61B 2017/07285* (2013.01); *A61B 2090/034* (2016.02); *A61B 2090/0812* (2016.02); *A61B 2090/0814* (2016.02)

(58) Field of Classification Search
CPC ..... A61B 90/03; A61B 17/068; A61B 17/105; A61B 17/32; A61B 2090/0801; A61B 2017/2946; A61B 17/8057
USPC .......................................... 227/175.1–182.1
See application file for complete search history.

(56) References Cited

U.S. PATENT DOCUMENTS

| | | | | |
|---|---|---|---|---|
| 4,930,674 | A * | 6/1990 | Barak | A61B 17/072 227/179.1 |
| 4,955,959 | A | 9/1990 | Tompkins et al. | |
| 5,129,570 | A * | 7/1992 | Schulze | A61B 17/07207 227/175.2 |
| 5,465,896 | A | 11/1995 | Allen et al. | |
| 9,498,215 | B2 * | 11/2016 | Duque | A61B 17/07207 |
| 9,924,941 | B2 * | 3/2018 | Burbank | A61B 17/068 |
| 2005/0222616 | A1 | 10/2005 | Rethy et al. | |
| 2010/0065604 | A1 * | 3/2010 | Weng | A61B 17/07207 227/175.2 |
| 2011/0068147 | A1 * | 3/2011 | Racenet | A61B 17/072 227/180.1 |
| 2013/0256375 | A1 * | 10/2013 | Shelton, IV | A61B 17/07207 227/176.1 |
| 2013/0327808 | A1 | 12/2013 | Chen et al. | |
| 2015/0173745 | A1 * | 6/2015 | Baxter, III | A61B 17/07207 227/175.3 |
| 2017/0027574 | A1 * | 2/2017 | Nalagatla | A61B 17/1155 |

FOREIGN PATENT DOCUMENTS

| | | |
|---|---|---|
| CN | 101991450 A | 3/2011 |
| CN | 101991453 A | 3/2011 |
| CN | 201768000 U | 3/2011 |
| CN | 102068290 A | 5/2011 |
| CN | 202446163 U | 9/2012 |
| CN | 102743201 A | 10/2012 |
| CN | 202982103 U | 6/2013 |
| CN | 203341779 A | 12/2013 |
| CN | 103720499 A | 4/2014 |
| CN | 203634231 U | 6/2014 |
| EP | 0373762 B1 | 1/1997 |
| JP | 06-121798 A | 5/1994 |
| JP | 10-000195 A | 1/1998 |
| JP | 2010063895 A | 3/2010 |
| JP | 2013534159 A | 9/2013 |

* cited by examiner

LINEAR CUTTING STAPLER

This appliction is a U.S. National Phase Of International Application No. PCT/CN2014/095149, filed Dec. 26, 2014, which claims priority to China Patent Application Nos. 201310749269.5, filed Dec. 31, 2013, and 201320887855.1, filed Dec. 31, 2013, the disclosures of which are all incorporated herein by reference.

TECHNICAL FIELD

The invention belongs to the technical field of medical apparatus and instruments and particularly relates to a linear cutting stapler.

BACKGROUND

Linear cutting staplers are widely used in surgical operations such as wound closure and the closure and excision of internal tissues. A typical linear cutting stapler as disclosed in U.S. Pat. No. 5,129,570 performs two functions of stapling and cutting, to remove the redundant tissues while stapling the wound. This kind of linear cutting stapler generally includes two jaws (i.e., an upper jaw and a lower jaw), closing handles (i.e., an upper handle and a lower handle) for closing the upper jaw and the lower jaw, an anvil and a staple cartridge arranged opposite to each other at the distal ends of the upper jaw and lower jaw respectively, a firing piece and a cutter pushing rod provided with a cutter at its distal end which are arranged in the staple cartridge and can simultaneously move relative to the staple cartridge, and a button for driving the firing piece and the cutter pushing rod to move. Staples are arranged inside the staple cartridge. The firing piece successively pushes the staple pushers in sequence which then push the staples to the anvil, and the cutter cuts off the tissues between the staple cartridge and the anvil.

In the prior art, the linear cutting stapler can be used repeatedly by replacing the staple cartridge. During clinical use, the tissues need to be cut and sutured more than once, thus the staple cartridge requires to be replaced repeatedly. That is to say, while the surgeon finishes one set of cutting and suturing actions, firstly, reset the stapler, and then open the upper jaw and the lower jaw; secondly, withdraw the stapler from the surgical spot and then replace the staple cartridge for the linear cutting stapler continuing the next set of cutting and suturing operations.

However, since some careless or inexperienced surgeons may fire the stapler without replacing the used staple cartridge, medical accidents will occur, namely, cutting the tissues without suture. To prevent such accidents from happening, a safety mechanism preventing the second firing action should be added in the linear cutting stapler to avoid medical accidents caused by the misoperation of surgeons.

SUMMARY

An object of the invention is to provide a linear cutting stapler, which can prevent the stapler from second firing action without replacing the used staple cartridge.

For realizing the above-mentioned objectives, the invention provides a linear cutting stapler comprising an upper jaw and a lower jaw capable of being closed or opened relative to each other, said upper jaw includes an anvil and said lower jaw includes a staple cartridge frame; said staple cartridge frame is detachably provided with a staple cartridge, a cutter pushing rod and a cutter disposed at the distal end of said cutter pushing rod are moveably arranged in said staple cartridge frame, said cutter is capable of moving from a proximal end to a distal end of said staple cartridge with the function of said cutter pushing rod to cut off target tissues between said anvil and said staple cartridge, wherein, said linear cutting stapler further comprises a safety piece mounted on said staple cartridge and being capable of moving upward and downward relative to said staple cartridge; said cutter comprises a slot capable of locking said safety piece and a contact part formed above said slot; while said cutter is placed at the proximal end of said staple cartridge and under an unlocked state, said safety piece is positioned at a first position where it is abutting with the upper wall of said contact part to avoid getting into said slot; after said cutter breaks away from said safety piece, said safety piece is at a free position; and said cutter is capable of returning back to the proximal end of said staple cartridge in the direction from the distal end to the proximal end of said staple cartridge to get into a locked state, said safety piece is positioned in a second position where it is stuck in said slot to restrict the movement of said cutter.

Preferably, said contact part extends from a distal end to a proximal end of said cutter, said cutter further comprises a stopper arranged at a proximal end of said slot, and while said safety piece is in the said slot, said safety piece abuts against said stopper if said cutter moves towards the distal end; a notch is formed between the proximal end of said contact part and said stopper and defined by said contact part, said stopper and said slot together, said safety piece is capable of getting into said slot via said notch.

Preferably, in the direction from the distal end to the proximal end of said cutter, the bottom wall of said contact part presents being upward sloped or parallel with the moving plane of said cutter.

Preferably, the upper wall of said contact part is parallel with the moving plane of said cutter, or presents being downward sloped in the direction from the distal end to the proximal end of said cutter.

Preferably, after said cutter breaks away from said safety piece, said safety piece is at said free position, said free position is higher or lower than or same height as said second position.

Preferably, the proximal end of said stopper is provided with a guiding part, said guiding part comprises a guiding surface for guiding said safety piece from said free position onto the upper wall of said stopper; in the direction from the proximal end to the distal end of said cutter, said guiding surface presents as an upward slope or a cambered surface with smooth transition.

Preferably, the proximal end of said guiding surface extends downwards to a position below said free position.

Preferably, said safety piece is made of deformable material and has elasticity in the vertical direction.

Preferably, the Rockwell Hardness HRC of said safety piece ranges between 28 degrees~35 degrees.

Preferably, the Rockwell Hardness HRC of said safety piece is 30 degrees.

Preferably, said safety piece is detachably mounted on said staple cartridge.

Preferably, a pair of side walls of said staple cartridge are respectively provided with a mounting hole for inserting said safety piece, and said mounting hole is a blind hole with its outer end closed.

Preferably, said linear cutting stapler further comprises a cutter sheath which is detachably mounted at the proximal end of said staple cartridge, said safety piece is detachably mounted inside the said cutter sheath, and the longitudinal axis of said safety piece along the length direction of safety piece is perpendicular to that of said staple cartridge.

Preferably, said cutter sheath comprises two opposite installation walls and an interconnection wall connecting between said two installation walls, said two installation walls are provided with a bump respectively, said staple cartridge is provided with a groove capable of being engaged with said bump.

Preferably, said two installation walls are respectively provided with an installation hole for inserting said safety piece, said installation hole is lower than the upper wall of said contact part, said safety piece is made of deformable material, and while said safety piece is abutting against the upper wall of said contact part, said safety piece is under forced deformation state.

Preferably, the dimension of said installation hole almost equals to or is slightly larger than the thickness of said safety piece.

Preferably, said installation hole is higher or same height as the bottom of said slot.

Preferably, the top of said stopper is higher than said installation hole, the proximal end of said stopper is provided with a guiding part, the proximal end of said guiding part is lower than said installation hole.

Preferably, said two installation walls are respectively provided with an installation hole for inserting said safety piece, said safety piece is made of rigid plate, the height dimensions of said installation hole allow said safety piece to ascend to the upper wall of said contact part and to descend to the upper wall of said stopper.

Compared with the prior art, the linear cutting stapler provided by the present invention comprises a special mechanism of the coordination between the safety piece and the cutter. After installation, the safety piece is abutted against the upper wall of the contact part of the cutter and won't fall into the slot below the contact part, thus, the safety piece is under the unlocked state, the cutter and firing piece can move from the proximal end to the distal end of the staple cartridge to finish the process of cutting and stapling. And, while the cutter is pulled back, the safety piece enters into the slot and gets stuck there, and then the safety piece can restrict the movement of the cutter to prevent the stapler from second firing action without replacing the staple cartridge, which can avoid medical accidents.

DETAILED DESCRIPTION

Hereinafter, embodiments are described in detail with reference to the accompanying drawings. However, these embodiments can't be used for limiting the scope of present invention. Any other equivalent deformations or modifications of structures, methods or functions which are made by the technical persons in the art according to these embodiments are all intended to be included in the scope of invention.

The terms describing places or directions in the description are determined by taking the position of operator as reference, wherein, the "proximal end" is the end close to the operator, and the "distal end" is the end far away from the operator.

Figure 1:
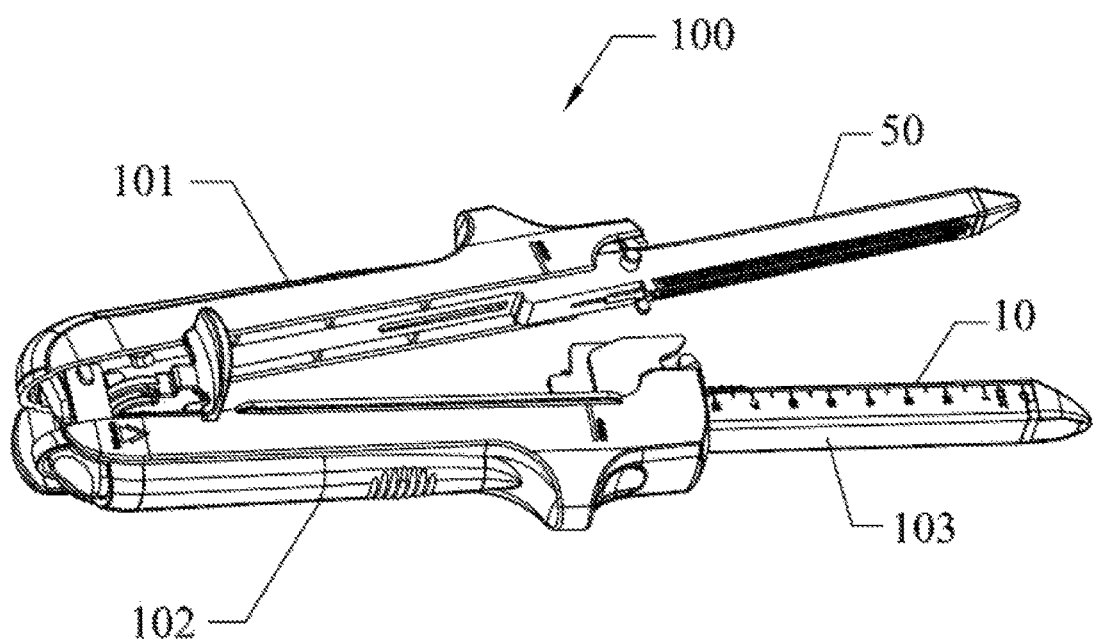
FIG. 1 is a view of a linear cutting stapler according to an embodiment of the present invention.
Figure 2:
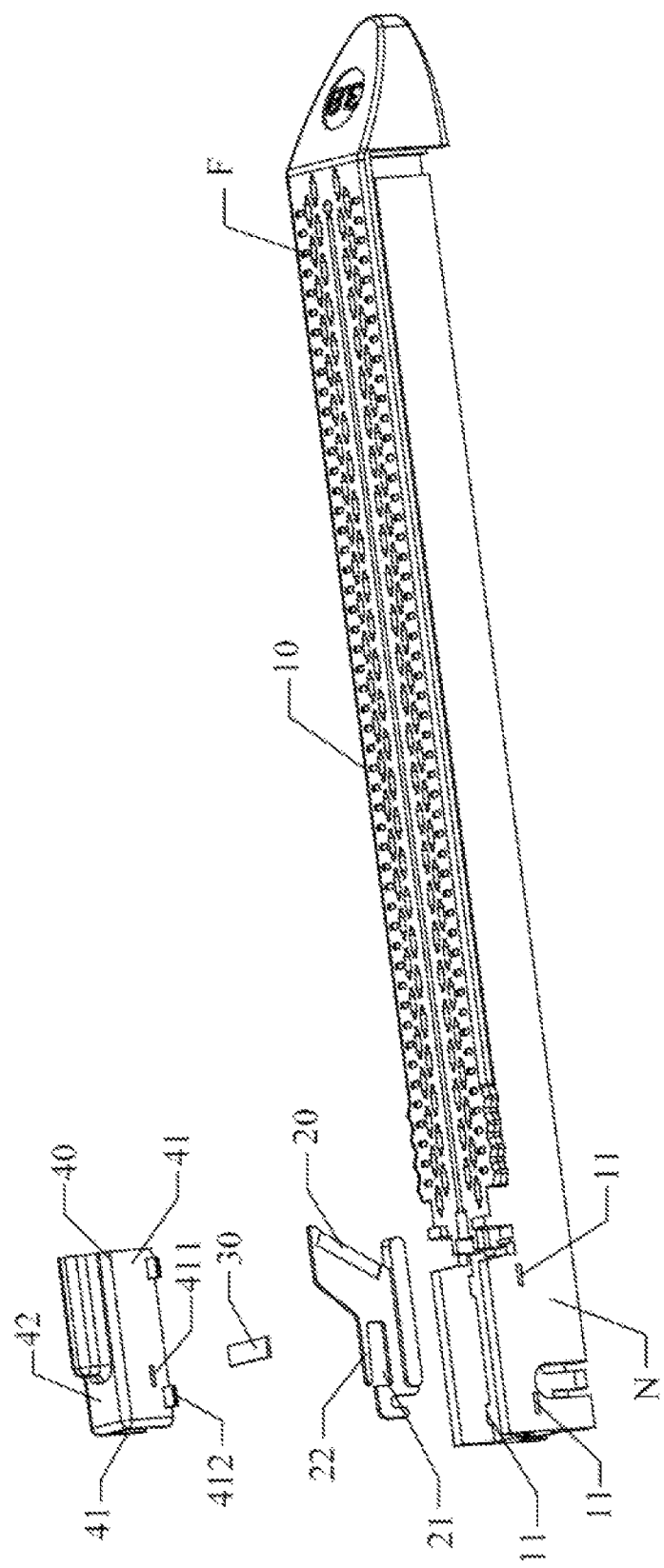
FIG. 2 is an exploded view of a linear cutting stapler according to an embodiment of the present invention.
Figure 3:
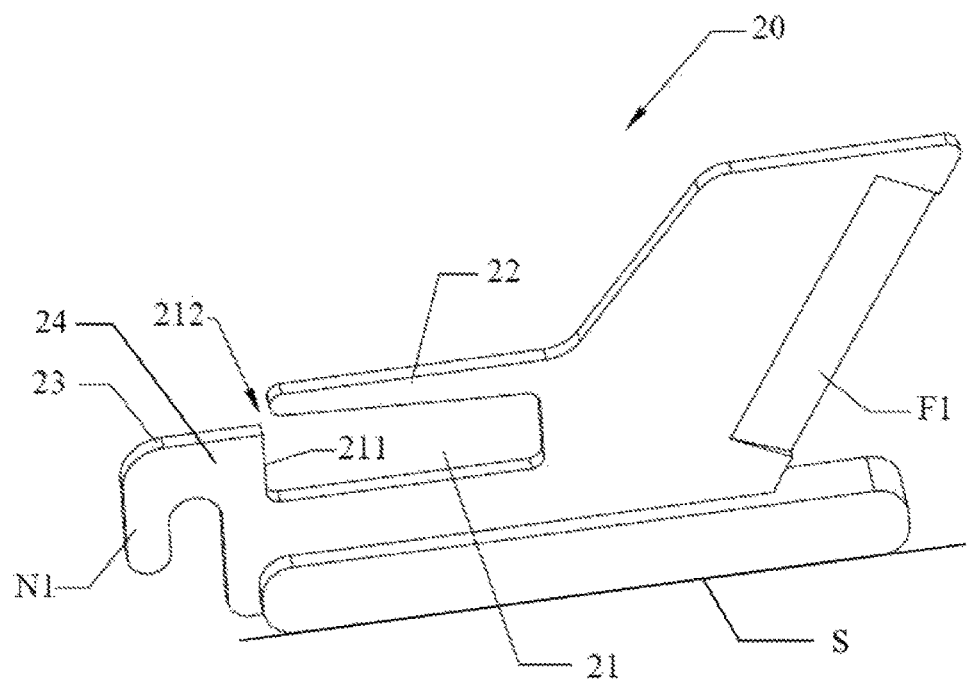
FIG. 3 is a view showing a cutter of a linear cutting stapler according to an embodiment of the present invention.
Figure 4:
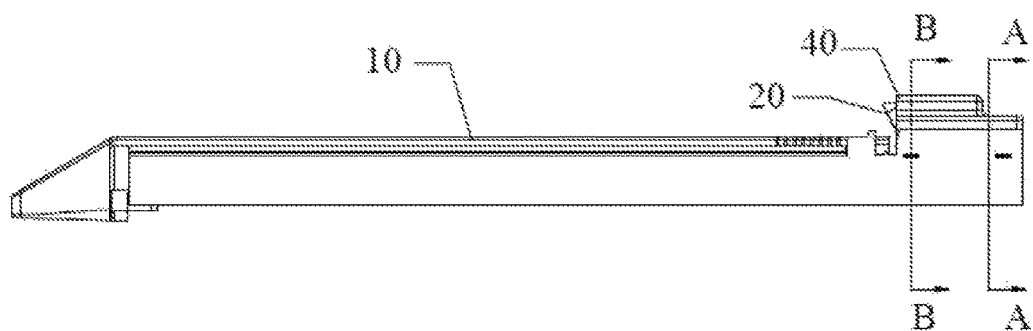
FIG. 4 is a view of a linear cutting stapler while its cutter has not been fired according to an embodiment of the present invention.

Referring to FIG. 1 and FIG. 2, a liner cutting stapler 100 according to one embodiment of present invention is presented. In this embodiment, the liner cutting stapler 100 comprises an upper jaw 101 and a lower jaw 102 capable of being closed or opened relative to each other. It should be explained that the terms such as "upper" and "lower" in this description are not intended to imply any absolute relationship of position, but merely for conveniently describing.

The upper jaw 101 comprises an anvil 50. The lower jaw 102 comprises a staple cartridge frame 103 which is detachably provided with a staple cartridge 10. The upper jaw 101 and the lower jaw 102 can be closed in relative to each other to clamp the target tissues between the anvil 50 and the staple cartridge 10. A cutter pushing rod (not shown) and a cutter 20 disposed at the distal end of the cutter pushing rod are moveably arranged in the staple cartridge frame 103. The cutter 20 is capable of moving from the proximal end N to the distal end F of the staple cartridge 10 by the function of the cutter pushing rod to cut off the target tissues between the anvil 50 and the staple cartridge 10. The bottom surface S of the cutter 20 is the moving plane S of the cutter 20 moving back and forth between the proximal end and the distal end of the staple cartridge 10.

The linear cutting stapler 100 further comprises a safety piece 30 arranged fixedly relative to the staple cartridge 10 in a certain direction (The description "arranged fixedly relative to the staple cartridge 10 in a certain direction" herein means the safety piece 30 is mounted on the staple cartridge 10 and capable of moving upward and downward relative to the staple cartridge 10). In this embodiment, the safety piece 30 is fixed with the staple cartridge 10 in the moving direction of the cutter 20, however, the safety piece 30 can move upward and downward relative to the staple cartridge 10, such as the deformation of safety piece 30 in the upward and downward direction.

In this embodiment, the longitudinal axis of safety piece 30 along the length direction of safety piece 30 is perpendicular to that of the staple cartridge 10. The safety piece 30 may be a thin elastic sheet. The safety piece 30 may be made of deformable material and easy to be bended in its thickness direction, but the present invention is not limited thereto.

The linear cutting stapler 100 comprises a cutter sheath 40 which is detachably mounted at the proximal end N of the staple cartridge 10. The cutter sheath 40 comprises two installation walls 41 and an interconnection wall 42 connecting between the two installation walls 41. The two installation walls 41 are respectively provided with an installation hole 411 for inserting the safety piece 30. The two ends of safety piece 30 are engaged with the installation holes 411 in two installation walls 41 so as to be mounted in the cutter sheath 40. The two installation walls 41 are provided with a bump 412 respectively, and the staple cartridge 10 is provided with a groove 11 engaged with the bump 412. The cutter sheath 40 may be made of deformable material, thus its installation can be performed by applying a counter-force onto the two installation walls 41 to engage the bumps 412 provided on the cutter sheath 40 into the groove 11, so as to fix the cutter sheath 40 with the staple cartridge 10. It should be explained that the fixation way of "bump and groove" by which the cutter sheath 40 and the staple cartridge 10 are fixed with each other is merely exemplary. In other alternative embodiments, same fixation effect can be realized by other ways such as arranging the groove in the cutter sheath 40 and bump on the staple cartridge 10. Besides, the way of mounting the safety piece 30 in the cutter sheath 40 which is described herein is just an exemplary example of mounting the safety piece 30 in the staple cartridge 10. In other variant embodiments, for example, the safety piece 30 can be directly mounted onto the side wall of the staple cartridge without the cutter sheath 40, a pair of side walls of the staple cartridge are respectively provided with a mounting hole for inserting the safety piece, and the mounting hole is a blind hole with its outer end closed.

Figure 5:
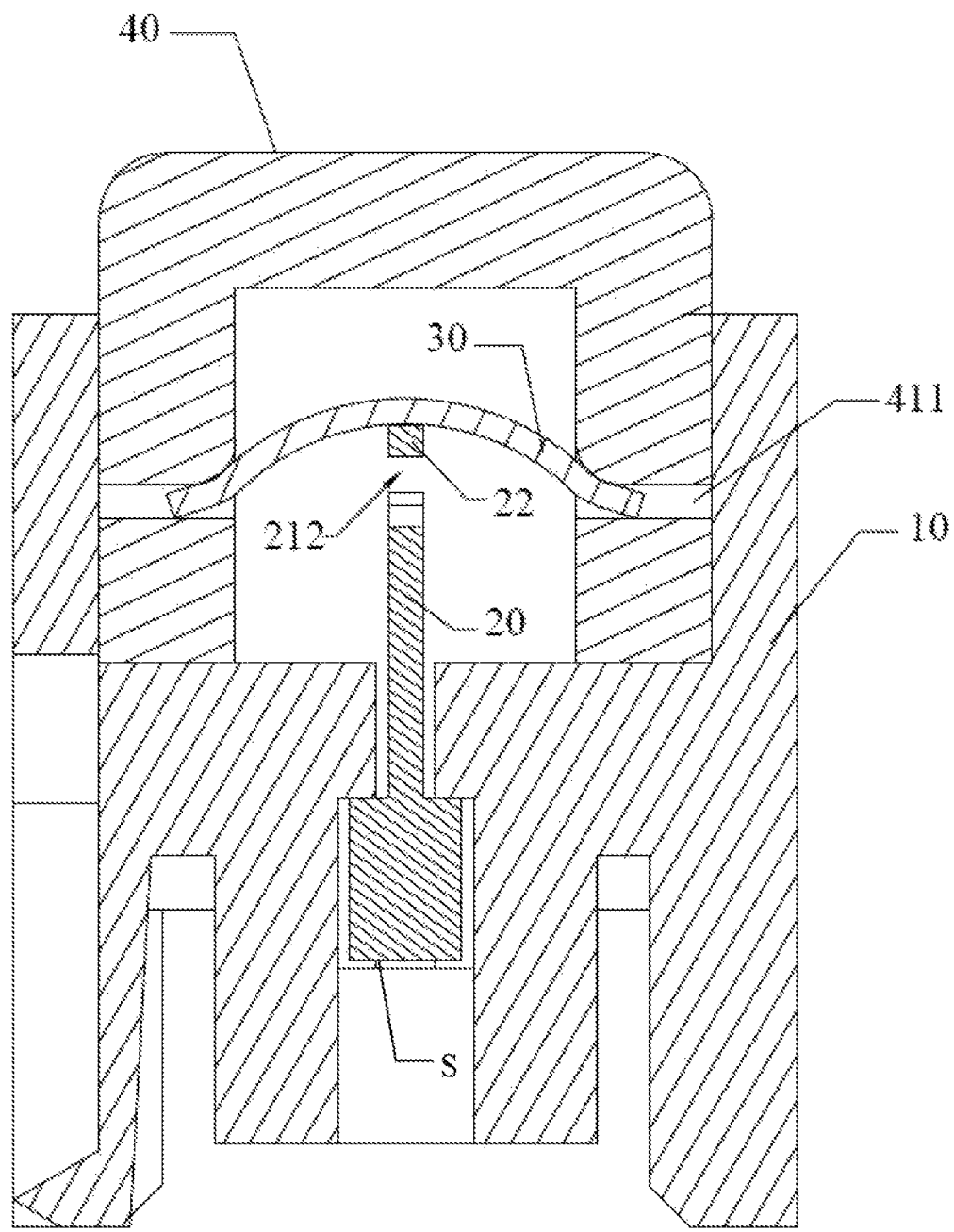
FIG. 5 is sectional view in A-A direction shown in FIG. 4.
Figure 8:
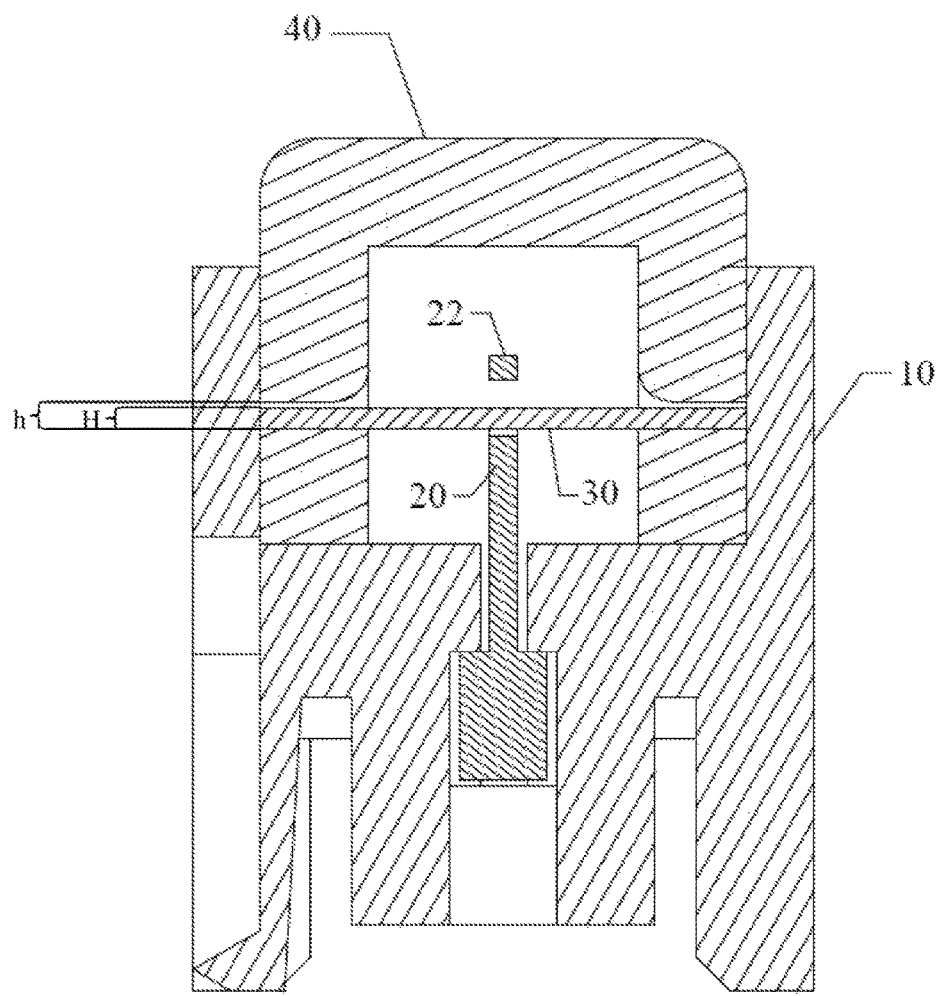
FIG. 8 is a sectional view in A-A direction shown in FIG. 7.

The cutter 20 comprises a slot 21 capable of restricting the safety piece 30. While the safety piece 30 is stuck in the slot 21, the movement of the cutter 20 is also restricted. The description herein about restricting the movement of the cutter means the cutter 20 can't be fired to cut off the tissues, and does not mean that the cutter should be fastened or fixed completely. A contact part 22 is formed above the slot 21. The upper wall of the contact part 22 can be abutting with the safety piece 30 to prevent the safety piece 30 from getting into the slot 21. While the cutter 20 is placed at the proximal end N of the staple cartridge 10, the safety piece 30 can be selectively positioned at the second position (as shown in FIG. 8, the safety piece 30 is stuck in the slot 21) or the first position (as shown in FIG. 5, the safety piece 30 is abutting with the upper wall of the contact part 22). Thus, if the staple cartridge 10 is not a used one, the safety piece 30 may be placed at the first position (namely, the safety piece 30 abutting against the upper wall of the contact part 22), the cutter 20 is under an unlocked state (or, under a standby state before firing), the surgeon can fire the stapler to complete the cutting and stapling actions on target tissues. If the staple cartridge 10 should be replaced or is returned to the proximal end N after firing, the safety piece 30 is placed at the second position (namely, the safety piece 30 is stuck in the slot 21 provided in the cutter 20), the cutter is under the locked state, thus the stapler can not be fired and the safety insurance preventing the second firing action is realized. Besides, while the cutter 20 leaves the proximal end N of staple cartridge 10, the safety piece 30 is at a free position after it breaks away from the cutter 20. In this embodiment, the free position is with a height corresponding to the bottom wall of staple cartridge 10 almost equal to that of the second position (after the safety piece 30 falls into the slot 21, the second position where the safety piece 30 is may be higher than or same height as the inner bottom wall of the slot 21). During the process of practical use, the safety piece 30 may be slightly deformed due to its own elasticity after breaking away from the contact part 22 of the cutter 20, which makes the free position a little higher than the second position. In other variant embodiments, the free position may be higher than the second position (but won't higher than the notch 22 described below). In other variant embodiments, the free position may be lower than the second position (namely, the height of inner bottom wall of the slot 21 corresponding to the bottom wall of staple cartridge 10 is higher than that of the free position).

The slot 21 of cutter 20 is capable of locking the safety piece 30, while the cutter 20 moving in the direction from the distal end F to the proximal end N of the staple cartridge 10. After the stapler has been fired once, the cutter should be pulled back from the distal end F of the staple cartridge 10. While the cutter 20 is pulled back to the proximal end N of the staple cartridge 10, the safety piece 30 enters into the slot 21 of the cutter 20 where it gets stuck. Such structure can prevent the second firing action while the staple cartridge has been already fired, and be more suitable for the practical operation requirements.

With reference to FIG. 3 to FIG. 6, the details of structure are as follows. The contact part 22 is extending from the distal end F1 to the proximal end N1 of the cutter 20. The contact part 22, together with the stopper 24 disposed at the proximal end N1 of the cutter 20, defines the slot 21 provided with the notch 212. The safety piece 30 can fit into the slot 21 via the notch 212. In this embodiment, the installation hole 411 is lower than the upper wall of the contact part 22 (namely, the installation hole 411 is closer to the bottom wall of the staple cartridge 10 than to the upper wall of the contact part 22), and the inner margin of upper wall of the installation hole 411 transits smoothly, of which such structure can be more suitable for the safety piece 30 with elastic deformation while the safety piece 30 is supported by the upper wall of contact part 22 (namely, the safety piece 30 is at the first position). The safety piece 30 may be a thin elastic sheet. The safety piece 30 may be made of deformable material and easy to be bended in its thickness direction, thus while the safety piece 30 is abutting against the upper wall of the contact part 22, the safety piece 30 is under a force deformation state in the first position.

The top of the stopper 24 (namely, the top of the side wall 211 of the slot 21 close to the notch 212) is higher than the installation hole 411. The distance between the top of stopper 24 and the bottom wall of the staple cartridge 10 is greater than that between the installation hole 411 and the bottom wall of the staple cartridge 10. Besides, the proximal end of the stopper 24 (namely, between the side wall 211 of the slot 21 close to the notch 212 and the proximal end N1 of the cutter 20) is provided with a guiding part 23. The proximal end of guiding part 23 is lower than the installation hole 411 (namely, the distance between the proximal end of guiding part 23 and the bottom wall of staple cartridge 10 is smaller than that between the installation hole 411 and the bottom wall of staple cartridge 10). Thus, while the cutter 20 is moving in the direction from the distal end F to the proximal end N of the staple cartridge 10, the safety piece 30 can be jacked up by engaging with the guiding part 23 and then gradually enter into the slot 21 through the top wall of the stopper 24, after that, the safety piece 30 is locked by the side wall 211 to prevent the second firing action.

In the embodiment, the guiding part 23 can guide the safety piece 30 from the free position onto the guiding surface on the top wall of the stopper 24. In the direction from the proximal end to the distal end, the guiding surface presents as an upward slope or a cambered surface with smooth transition. The cambered surface with smooth transition may be an upward protruding arc surface, or a downward protruding arc surface with its guiding end formed like a hook, or a wavy cambered surface with smooth transition. The proximal end of guiding surface is extending downward to a position below the free position, which better ensures that the guiding surface can guide the safety piece 30 to move upward and over the stopper 24, after the guiding surface contacts the safety piece 30.

In this embodiment, the safety piece 30 may be a thin elastic sheet or made of deformable material and have elasticity in its thickness direction. Besides, the safety piece 30 requires hardness with certain degree. The hardness degree should not be too large, otherwise the safety piece 30 may not be easily deformed to be jacked up to the first position. And the hardness degree should not be too small, otherwise the safety piece 30 may be deformed plastically at the first position and may not return back to its original form after it leaves the first position, which may cause the safety piece 30 can not easily enter into the notch 212 to realize the function of preventing the second firing action.

As a preferred embodiment, the Rockwell Hardness (HRC) of the safety piece ranges between 28 degrees~35 degrees. More preferably, the Rockwell Hardness (HRC) of the safety piece is 30 degrees.

As a preferred embodiment, the distance between the installation hole 411 and the bottom wall of staple cartridge 10 is greater than that between the bottom wall of the slot 21 and the bottom wall of the staple cartridge 10, and the guiding part 23 may be downward sloped in the extending direction from the distal end F1 to the proximal end N1 of the cutter 20 for better guiding the safety piece 30. In this direction, the bottom wall of contact part 22 may be upward sloped (namely, the distance between the bottom wall of contact part 22 and the bottom wall of slot 21 is gradually increase), to coordinate with the guiding part 23 to guide the safety piece 30 into the slot 21 more smoothly. Preferably, in this direction, the upper wall of the contact part 22 is parallel with the moving plane S of the cutter 20 (the thickness of the contact part 22 is gradually decreased, however, the distance between the upper wall of contact part 22 and the bottom of slot 21 remains unchanged), thus, while the stapler is tired, the firing guide will be more stable and won't cause hindrance in the moving path of cutter 20.

In other variant embodiments, the bottom wall of contact part 22 is parallel with the moving plane S of the cutter 20 in the extending direction from the distal end F1 to the proximal end N1 of the cutter 20. In other variant embodiments, the upper wall of the contact part 22 is slightly downward sloped in the extending direction from the distal end F1 to the proximal end N1 of the cutter 20, and the safety piece 30 will break away from the contact part 22 of the cutter successfully.

Figure 6:
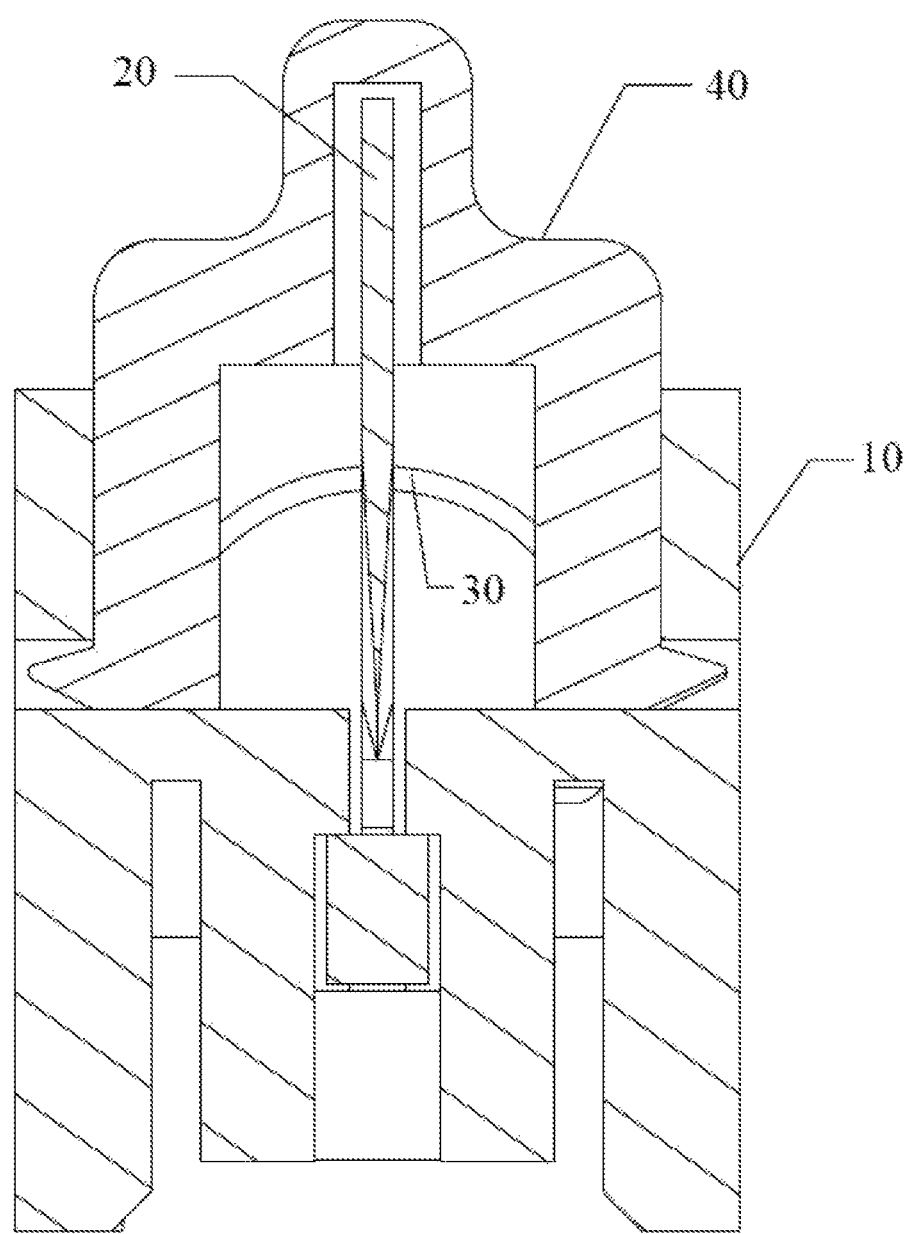
FIG. 6 is a sectional view in B-B direction shown in FIG. 4.
Figure 7:
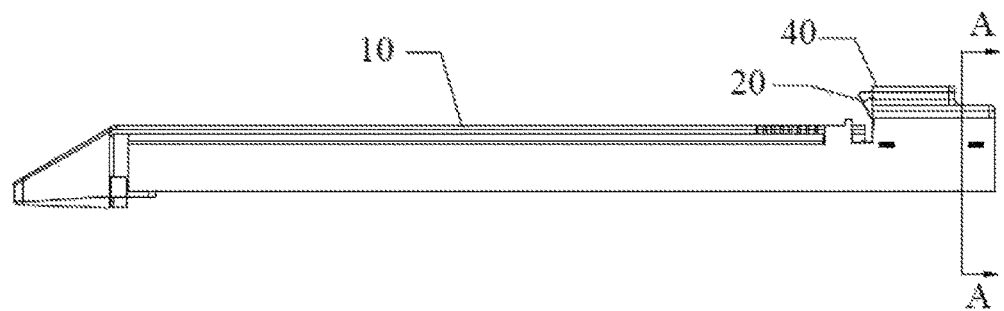
FIG. 7 is a view of a linear cutting stapler, while its cutter has been fired and withdrawn to the proximal end of staple cartridge, according to an embodiment of the present invention.

With reference to FIG. 5 to FIG. 8, the detailed operational processes of the stapler are as follows. Firstly, inserting the safety piece 30 into the cutter sheath 40 to fix the safety piece 30, and mounting the cutter 20 to the proximal end N of the staple cartridge 10; secondly, buckling up the cutter sheath 40 and the staple cartridge 10 to make the safety piece 30 being abutted against the contact part 22 of the cutter 20, with which the safety piece 30 is forced to have an upward bent deformation (as shown in FIGS. 5 and 6); after the cutter 20 is fired to move, the safety piece 30 is under the free state after it returns back to original shape with its own restoring force; while the one process of cutting and stapling is finished, pulling back the cutter 20 from the distal end F towards the proximal end N of the stapler cartridge 10, then the safety piece 30 is guided by the guiding part 23 of the cutter 20 to rise up a little and subsequently get over the stopper 24 and gradually fall into the slot 21 where it is stuck finally, so as to realize the restricting function on the cutter 20 and prevent the second firing action of the stapler.

The linear cutting stapler provided by present invention, of which the structure is simple and the operation is convenient, can prevent the stapler from second firing action without replacing the staple cartridge through a special mechanism of the coordination between the safety piece and the cutter, to avoid medical accidents.

Other Variant Embodiment

In the embodiment shown in FIG. 5 to FIG. 8, the height h of the installation hole 411 almost equals to the thickness H of the elastic safety piece 30 (with reference to FIG. 8).

However, in other variant embodiments, the safety piece 30 may be rigid plate, the height dimensions of the installation hole allow the safety piece 30 to ascend to the upper wall of the contact part 22 and to descend to below the upper wall of stopper 24.

It should be understood that although the description is presented in accordance with these embodiments, but not every embodiment contains only a single technical solution, only for the sake of clarity. Those skilled in the art should take the description as a whole to combine technical solutions in these embodiments to form the other embodiments which can be understood.

A series of detailed instructions listed above are merely a specific description for the practical embodiments of present invention, which are not intended to limit the scope of the present invention. All the equivalent embodiments or variants without departing away from the spirit of present invention should be included within the scope of the present invention.

What is claimed is:

1. A linear cutting stapler, comprising an upper jaw and a lower jaw capable of being closed or opened relative to each other, said upper jaw includes an anvil and said lower jaw includes a staple cartridge frame; a staple cartridge is detachably arranged on said staple cartridge frame, a cutter pushing rod and a cutter disposed at the distal end of said cutter pushing rod are movably arranged in said staple cartridge frame, said cutter is capable of moving from a proximal end to a distal end of said staple cartridge with the function of said cutter pushing rod to cut off target tissues between said anvil and said staple cartridge, wherein:

said linear cutting stapler further comprises a safety piece mounted on said staple cartridge and being capable of moving upward and downward relative to said staple cartridge; said cutter comprises a slot capable of receiving said safety piece and a contact part formed above said slot; while said cutter is placed at the proximal end of said staple cartridge and not locked by said safety piece, said safety piece is positioned at a first position where it is abutting with an upper wall of said contact part to avoid getting into said slot; after said cutter moves from the proximal end towards the distal end of said staple cartridge, said contact part is separated from said safety piece, said safety piece moves downwards to be at a free position; and said cutter is capable of returning back to the proximal end of said staple cartridge in the direction from the distal end to the proximal end of said staple cartridge to be locked by said safety piece, said safety piece is positioned in a second position where it is stuck in said slot to restrict the movement of said cutter.

2. The linear cutting stapler according to claim 1, wherein, said contact part extends from a distal end to a proximal end of said cutter, said cutter further comprises a stopper arranged at a proximal end of said slot, and while said safety piece is in the said slot, said safety piece abuts against said stopper if said cutter moves towards the distal end; a notch is formed between the proximal end of said contact part and said stopper and defined by said contact part, said stopper and said slot together, said safety piece is capable of getting into said slot via said notch.

3. The linear cutting stapler according to claim 2, wherein, in the direction from the distal end to the proximal end of said cutter, the bottom wall of said contact part presents being upward sloped or parallel with the moving plane of said cutter.

4. The linear cutting stapler according to claim 3, wherein, the upper wall of said contact part is parallel with the moving plane of said cutter, or presents being downward sloped in the direction from the distal end to the proximal end of said cutter.

5. The linear cutting stapler according to claim 2, wherein, after said cutter breaks away from said safety piece, said safety piece is at said free position, said free position is higher or lower than or same height as said second position.

6. The linear cutting stapler according to claim 5, wherein, the proximal end of said stopper is provided with a guiding part, said guiding part comprises a guiding surface for guiding said safety piece from said free position onto the upper wall of said stopper; in the direction from the proximal end to the distal end of said cutter, said guiding surface presents as an upward slope or a cambered surface with smooth transition.

7. The linear cutting stapler according to claim 6, wherein, the proximal end of said guiding surface extends downwards to a position below said free position.

8. The linear cutting stapler according to claim 1, wherein, said safety piece is made of deformable material and has elasticity in the vertical direction.

9. The linear cutting stapler according to claim 1, wherein, the Rockwell Hardness HRC of said safety piece ranges between 28 degrees ~35 degrees.

10. The linear cutting stapler according to claim 9, wherein, the Rockwell Hardness HRC of said safety piece is 30 degrees.

11. The linear cutting stapler according to claim 1, wherein, said safety piece is detachably mounted on said staple cartridge.

12. The linear cutting stapler according to claim 11, wherein, a pair of side walls of said staple cartridge are respectively provided with a mounting hole for inserting said safety piece, and said mounting hole is a blind hole with its outer end closed.

13. The linear cutting stapler according to claim 1, further comprises a cutter sheath which is detachably mounted at the proximal end of said staple cartridge, said safety piece is detachably mounted inside the said cutter sheath, and the longitudinal axis of said safety piece along the length direction of safety piece is perpendicular to that of said staple cartridge.

14. The linear cutting stapler according to claim 13, wherein, said cutter sheath comprises two opposite installation walls and an interconnection wall connecting between said two installation walls, said two installation walls are provided with a bump respectively, said staple cartridge is provided with a groove capable of being engaged with said bump.

15. The linear cutting stapler according to claim 14, wherein, said two installation walls are respectively provided with an installation hole for inserting said safety piece, said installation hole is lower than the upper wall of said contact part, said safety piece is made of deformable material, and while said safety piece is abutting against the upper wall of said contact part, said safety piece is under forced deformation state.

16. The linear cutting stapler according to claim 15, wherein, the dimension of said installation hole almost equals to or is slightly larger than the thickness of said safety piece.

17. The linear cutting stapler according to claim 15, wherein, said installation hole is higher or same height as the bottom of said slot.

18. The linear cutting stapler according to claim 15, wherein, the top of said stopper is higher than said installation hole, the proximal end of said stopper is provided with a guiding part, the proximal end of said guiding part is lower than said installation hole.

19. The linear cutting stapler according to claim 14, wherein, said two installation walls are respectively provided with an installation hole for inserting said safety piece, said safety piece is made of rigid plate, the height dimensions of said installation hole allow said safety piece to ascend to the upper wall of said contact part and to descend to the upper wall of said stopper.

\* \* \* \* \*